United States Patent [19]

Panitz et al.

[11] Patent Number: 5,159,107
[45] Date of Patent: Oct. 27, 1992

[54] CONTINUOUS PREPARATION OF ALKYL PENTENOATES

[75] Inventors: Paul Panitz, Worms; Heinrich Reitz, Mannheim; Gunter Schuch, Ludwigshafen; Wilfried Seyfert, Weisenheim, all of Fed. Rep. of Germany

[73] Assignee: BASF Akteingesellschaft, Ludwigshafen, Fed. Rep. of Germany

[21] Appl. No.: 784,138

[22] Filed: Oct. 29, 1991

Related U.S. Application Data

[63] Continuation of Ser. No. 312,387, Feb. 17, 1989, abandoned, which is a continuation of Ser. No. 116,878, Nov. 5, 1987, abandoned.

[30] Foreign Application Priority Data

Nov. 8, 1986 [DE] Fed. Rep. of Germany ....... 3638218

[51] Int. Cl.$^5$ ..................... C07C 67/38; C07C 69/533
[52] U.S. Cl. ..................................... 560/206; 560/204
[58] Field of Search ......................... 560/205, 206, 207

[56] References Cited

U.S. PATENT DOCUMENTS

| | | | |
|---|---|---|---|
| 3,976,670 | 8/1976 | Fanning | 260/410.9 R |
| 4,259,520 | 3/1981 | Kummer et al. | |
| 4,360,692 | 11/1982 | Kummer et al. | 560/206 |
| 4,502,992 | 3/1985 | Hofmann et al. | 260/410.9 R |
| 4,586,987 | 5/1986 | Schneider et al. | |

*Primary Examiner*—Vivian Garner
*Attorney, Agent, or Firm*—Keil & Weinkauf

[57] ABSTRACT

A process for the continuous preparation of alkyl pentenoates comprises the following steps:
a) reaction of a butadiene-containing $C_4$ cut with an alkanol and carbon monoxide in the presence of a cobalt carbonyl catalyst and heterocyclic aromatic tertiary nitrogen base at from 100° to 160° C. and under from 100 to 1,200 bar and
b) treatment of the resulting reaction mixture, at the rate at which it is obtained, in a treatment zone, at from 100° to 160° C. under from 250 to 1,200 bar with a residence time of from 5 to 60 minutes, substantially without back-mixing.

9 Claims, No Drawings

CONTINUOUS PREPARATION OF ALKYL PENTENOATES

This application is continuation of application Ser. No. 07/312,387, filed on Feb. 17, 1989, which is a continuation of Ser. No. 07/116,878, filed Nov. 5, 1987, now abandoned.

The present invention relates to a process for the continuous preparation of alkyl pentenoates by reacting a butadiene-containing $C_4$ cut with an alkanol and carbon monoxide in the presence of a cobalt carbonyl catalyst and a heterocylic aromatic tertiary nitrogen base at from 100 to 160° C. and under from 400 to 1,200 bar.

German Laid-Open Application DOS 3,413,448 discloses a process for the preparation of alkyl pentenoates, in which butadiene-containing $C_4$ cuts are reacted with carbon monoxide and alkanols in the presence of cobalt carbonyl catalysts and tertiary nitrogen bases, and the liquid reaction mixture freed from excess carbon monoxide is treated with hydrogen at elevated temperatures under from 5 to 80 bar. Although, when hydrogen acts for a sufficiently long time, this procedure makes it possible to convert the cobalt carbonyl catalysts used into a nonvolatile form, so that substantial cobalt deposits are avoided during further working up, this process has the disadvantage that the pentenoates produced are partially hydrogenated. The olefins present in the residual hydrocarbons are also partially hydrogenated and are thus of less use subsequently. In another process described in German Laid-Open Application DOS 2,802,580, the reaction mixtures obtained in the preparation of alkyl pentenoates from butadiene-containing $C_4$ cuts by carbalkoxylation are treated with carbon monoxide at from 100 to 160° C. and under from 50 to 200 bar after the $C_4$ hydrocarbons and the uncovered butadiene have been separated off. The process has the disadvantage that the hydrocarbons removed contain substantial amounts of volatile cobalt catalyst which decomposes during the distillation. The blockages of the distillation columns which this causes then necessitates expensive flushing of the column, in which the cobalt is recovered in an inactive form.

It is an object of the present invention to design the preparation of alkyl pentenoates by carbalkoxylation of butadiene-containing $C_4$ cuts in such a way that the yield of alkyl pentenoates is not reduced, and the cobalt catalyst is converted to a nonvolatile form so that very little cobalt is deposited in the distillation during working up.

We have found that this object is achieved by a continuous process for the preparation of alkyl pentenoates by reacting a butadiene-containing $C_4$ cut with an alkanol and carbon monoxide in the presence of a cobalt carbonyl catalyst and a heterocyclic aromatic tertiary nitrogen base at from 100 to 160° C. and under from 100 to 1,200 bar, wherein the resulting reaction mixture is passed, at the rate at which it is obtained, through a treatment zone, at from 100 to 160° C. under from 250 to 1,200 bar with a residence time of from 5 to 60 minutes, substantially without back-mixing.

The novel process has the advantages that the deposition of cobalt during working up of the reaction mixture is substantially reduced and the yield of alkyl pentenoates is not adversely affected.

According to the invention, a butadiene-containing $C_4$ cut is used as a starting material. Mixtures defined as $C_4$ cuts are all mixtures of predominantly straight-chain $C_4$ hydrocarbons which contain more than 10% by weight of butadiene and more than 15% by weight of butenes. Depending on the source, the individual components are usually present in such mixtures in the following proportions:

butadiene from 10 to 70, on average from 30 to 60, % by weight isobutene from 15 to 40, on average from 20 to 35, % by weight but-1-ene from 10 to 40, on average from 10 to 25, % by weight but-2-ene from 5 to 20, on average from 5 to 15, % by weight butanes from 1 to 10, on average from 1 to 10, % by weight butynes from 0.1 to 3, on average from 0.1 to 3, % by weight.

Such $C_4$ cuts are obtained, for example, in the dehydrogenation of butane or butene, or as byproducts in the production of ethylene by thermal cleavage (cracking) of liquified natural gas (LNG), naphtha or higher hydrocarbon cuts.

$C_1$–$C_{14}$-alkanols, such as methanol, ethanol, propanol, butanol or isobutanol, are preferably used, methanol being particularly preferably employed. Advantageously, the alkanol is used in excess, in particular in an amount of from 1.1 to 5 moles per mole of butadiene.

Carbon monoxide is advantageously used in excess, for example from 1.5 to 10 times the stoichiometric amount.

The reaction is carried out at from 100 to 160° C., in particular from 120 to 145° C., a pressure of from 100 to 1,200, advantageously from 400 to 1,200, in particular from 500 to 900, bar being maintained.

The cobalt carbonyl catalysts used may be prepared in situ from cobalt salts, for example cobalt salts of fatty acids, such as formate, acetate, propionate or butyrate. The catalyst is advantageously introduced in the form of cobalt carbonyl itself. In particular, it has proven useful if the cobalt carbonyl catalyst dissolved in the $C_4$ cut is introduced into the reaction mixture. A solution of this type is obtained, for example, by reacting an aqueous solution of a cobalt salt of a fatty acid with a mixture of carbon monoxide and hydrogen in the presence of active carbon at from 100 to 170° C. and under from 100 to 400 bar. The resulting cobalt carbonyl is then extracted from the aqueous solution with butadiene-containing $C_4$ cut. Some of the cobalt carbonyl catalyst recovered is advantageously reused for the reaction.

As a rule, from 0.02 to 0.2 mole of cobalt carbonyl catalyst is used per mole of butadiene.

Suitable heterocyclic aromatic tertiary nitrogen bases advantageously have a $pK_a$ of from 4 to 9. Examples of suitable nitrogen bases are pyridine, 3-methyl-pyridine, 4-methylpyridine, 2,3-dimethylpyridine, 2,4-dimethylpyridine, 3,5-dimethylpyridine, 4-benzylpyridine, quinoline and isoquinoline. Pyridine and 3- and 4-methylpyridine and mixtures of these are particularly preferably used. It has proven advantageous to employ from 0.5 to 3 moles of the stated nitrogen bases per mole of butadiene.

The reaction can be carried out in one or more, for example from 1 to 4, reaction zones connected in series. The reaction mixture obtained contains, in addition to unconverted butadiene, other $C_4$ hydrocarbons from $C_4$ cut, heterocyclic aromatic tertiary nitrogen bases, cobalt carbonyl catalyst, unconverted alkanols, the alkyl pentenoates, which are the desired products, and by-products, such as valerates, vinylcyclohexene and polymers of butadiene.

In the novel process, the resulting reaction mixture is passed, at the rate at which it is removed from the first stage, through a treatment zone as a second stage, substantially without back-mixing. This reaction zone advantageously contains baffles, such as packing or trays with nozzle orifices, in order to avoid back-mixing. The treatment is carried out at from 100 to 160° C., in particular from 120 to 145° C., and under from 250 in particular from 500 to 900, bar. Furthermore, a residence time of from 5 to 60, in particular from 10 to 30 minutes is maintained in the treatment zone, which is preferably tubular. The reaction mixture from the first stage is advantageously passed through the treatment zone under the pressure and temperature conditions maintained in the first stage, without removal of reactants or reaction products. However, it is also possible to carry out the reaction at temperatures which differ from those of the first reaction zone and/or lower pressure.

Carbon monoxide is separated off from the mixture discharged from the second stage, and the liquid portions are worked up by distillation.

The alkyl pentenoates obtainable by the process of the invention are useful for the preparation of alkyl adipates by carbalkoxylation.

The Examples which follow illustrate the invention.

EXAMPLE

In an apparatus consisting of two stirred kettles having a capacity of 150 ml and connected in series, a mixture of 38 g/hour of $C_4$ cut containing 42% by weight of butadiene, 10.3 g/hour of methanol, 25 L (S.T.P.)/hour of carbon monoxide, 3.6 g/hour of dicobalt octacarbonyl and 33 g/hour of picoline is fed to the first kettle. The reaction in both stirred kettles is carried out at 135° C. and under 650 bar. Downstream of the second stirred kettle, the reaction mixture flows through a treatment zone having a diameter of 1.7 cm and a length of 16 cm. The tubular treatment zone is maintained at 135° C. and under 650 bar. The residence time is 15 minutes. The reaction mixture thus obtained is cooled and let down. It contains only 400 ppm of volatile cobalt, 200 ppm of which are deposited as metallic cobalt when the reaction products and reactants are separated off by distillation.

COMPARATIVE EXAMPLE

If Example 1 is repeated with the difference that the reacted mixture obtained after the carbalkoxylation is fed without further treatment directly for separation by distillation, the reacted mixture contains 2,100 ppm of Co in the form of volatile compounds, 1,500 ppm of which are deposited in the columns.

We claim:

1. A process for the continuous preparation of an alkyl pentenoate, which consists essentially of the following steps:
    a) reaction of a butadiene-containing $C_4$ cut with an alkanol and carbon monoxide in the presence of a cobalt carbonyl catalyst and a heterocyclic aromatic tertiary nitrogen base at from 100 to 160° C. and under from 100 to 1,200 bar,
    b) passing the resulting reaction mixture, which consists essentially of pentenoic acid alkyl esters, alkanols, residual hydrocarbons, carbon monoxide, a cobalt carbonyl catalyst, a heterocyclic aromatic tertiary nitrogen base and byproducts, at the rate at which it is obtained, through a treatment zone without the removal of reactants or reaction products and without the addition of additional reactants and molecular oxygen, at from 100 to 160° C. under from 250 to 1,200 bar with a residence time of from 5 to 60 minutes, substantially without back-mixing, and thereafter,
    c) separating off carbon monoxide from the mixture discharged from step (b) and working up the liquid portions of the discharged mixture by distillation, whereby the amount of cobalt distilled off in (c) is substantially reduced due to the treatment of the reaction mixture in step (b).

2. The process of claim 1, wherein pyridine, 3-methylpyridine or 4-methylpyridine or a mixture of these is used as the heterocyclic aromatic tertiary nitrogen base.

3. The process of claim 1, wherein from 0.5 to 3 moles of heterocyclic aromatic tertiary nitrogen base are used per mole of butadiene.

4. The process of claim 1, wherein from 0.02 to 0.2 mole of cobalt catalyst is used per mole of butadiene.

5. The process of claim 1, wherein a residence time of from 10 to 30 minutes is maintained in the treatment in stage b).

6. The process of claim 1, wherein the treatment in stage b) is carried out in a tubular treatment zone.

7. The process of claim 1, wherein the temperature in the treatment zone in step (b) is maintained at 120–145° C., the pressure in the zone is 500 to 900 bar and the residence time of the reaction mixture in the treatment zone is from 10 to 30 minutes.

8. The process of claim 1, wherein the treatment zone contains baffles to avoid back-mixing.

9. The process of claim 1, wherein the alkanol is used in an amount of from 1.1 to 5 moles per mole of butadiene.

* * * * *